United States Patent [19]

Kaslow et al.

[11] Patent Number: 5,853,739
[45] Date of Patent: Dec. 29, 1998

[54] TRANSMISSION-BLOCKING VACCINE AGAINST MALARIA

[75] Inventors: David C. Kaslow, Kensington, Md.; Philip J. Barr, Oakland, Calif.

[73] Assignees: The United States of America as represented by the Department of Health and Human Services, Washington, D.C.; Chiron Corporation, Emeryville, Calif.

[21] Appl. No.: 365,997

[22] Filed: Dec. 29, 1994

Related U.S. Application Data

[60] Continuation of Ser. No. 11,039, Jan. 29, 1993, abandoned, which is a division of Ser. No. 697,275, May 8, 1991, Pat. No. 5,217,898, which is a continuation-in-part of Ser. No. 658,845, Feb. 22, 1991, abandoned, which is a continuation-in-part of Ser. No. 188,918, May 2, 1988, abandoned.

[51] Int. Cl.$^6$ .................. A61K 39/015; C12N 15/00; C12N 7/00; C12P 21/02
[52] U.S. Cl. .................. 424/268.1; 424/184.1; 424/185.1; 424/272.1; 530/350; 435/69.1; 435/69.3; 435/69.9; 435/71.1; 435/255
[58] Field of Search .................. 424/272.1, 184.1, 424/268.1, 185.1; 435/69.1, 69.3, 69.9; 530/350

[56] References Cited

U.S. PATENT DOCUMENTS

| | | | |
|---|---|---|---|
| 4,546,082 | 10/1985 | Kurjan et al. | 435/172.3 |
| 4,826,957 | 5/1989 | Nussenzweig et al. | 530/350 |

OTHER PUBLICATIONS

Kaslow Immunology letters 25:83–86, 1990.
Bathurst et al., The 38th Annual Meeting of the American Society of Tropical Medicine & Hygiene. Dec. 10–14, 1989, p. 190 Abst. #218.
Mitchell, G.M. Parasitology, vol. 98, pp. 529–547 (1989).
Rawlings et al J. Exp Med. vol. 176, pp. 1483–1487 (1992).
Kaslow Abstract from Molecular Parasitology Meeting, Sept. 9–12 (1990).
Gibson et al Abstract from The 38$^{th}$ Annual Meeting of The Am Soc. of Trop. Med & Hyg. Dec. 10–14 1989.
Kaslow et al Nature vol. 333 pp. 74–76 (1988).
Abrignan et al Proc. Nat'l Acad Sci USA vol. 87 pp. 6136–6140 (1990).
Miller et al. Science vol. 234 pp. 1349–1356 (1986).
Brake et al. Proc Nat'l Acad Sci USA vol. 81 pp. 4642–4644 (1984).
Gwadz et al. Infect. Immun. vol. 44 pp. 137–140 (1984).
Kaslow et al Vaccine Research vol. 2 pp. 95–103 (1993).
Kaslow Vaccine Research vol. 2 pp. 197–205 (1993.
Cox TIB TECH vol. 9 pp. 389–394 (1991).

*Primary Examiner*—Hazel F. Sidberry
*Attorney, Agent, or Firm*—Townsend and Townsend and Crew

[57] ABSTRACT

The present invention relates to transmission-blocking vaccines against malaria. Vaccines of the present invention contain a recombinant Pfs25 *Plasmodium falciparum* protein produced by yeast cells and to yeast cells producing the protein. Mice and monkeys inoculated with the yeast-expressed Pfs25 of the present invention have developed antibodies with transmission-blocking activity. The present invention also relates to methods of preventing or treating malarial infections using the vaccines of the present invention.

13 Claims, 3 Drawing Sheets

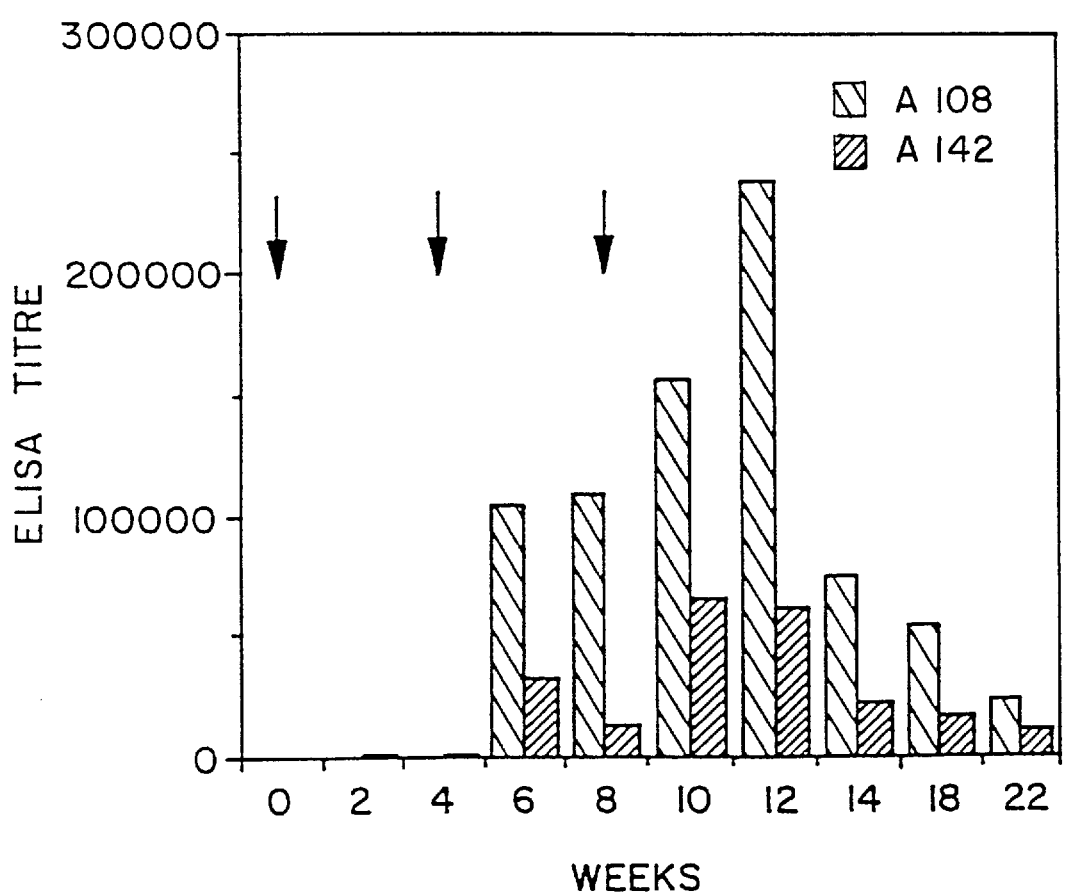

TRANSMISSION-BLOCKING VACCINE AGAINST MALARIA

The present application is a continuation of application Ser. No. 08/011,039, filed Jan. 29, 1993 now abandoned, which is itself a division of Ser. No. 07/697,275, filed May 8, 1991 now U.S. Pat. No. 5,217,898, which is itself a continuation-in-part of Ser. No. 07/658,845, filed Feb. 22, 1991, which is itself a continuation-in-part of Ser. No. 07/188,918, filed May 2, 1988, both abandoned.

BACKGROUND OF THE INVENTION

1. Field of the Invention

The present invention relates to transmission-blocking vaccines against malaria and methods of preventing the transmission of the disease.

2. Background Information

The *Plasmodium falciparum* parasite is the major cause of malaria in humans. The life cycle of the parasite begins in man when young malarial parasites or "sporozoites" are injected into the bloodstream of a human by the mosquito. After injection the parasite localizes in liver cells from which after approximately one week, the parasites or "merozoites" are released into the bloodstream. The entry of the parasites into the bloodstream begins the "erythrocytic" phase. Each parasite enters the red blood cell in order to grow and develop. When the merozoite matures in the red blood cell, it is known as a trophozoite and schizont. A schizont is the stage when nuclear division occurs to form individual merozoites which are released to invade other red cells. After several schizogonic cycles, some parasites, instead of becoming schizonts through asexual reproduction, develop into large uninucleate parasites. These parasites undergo sexual development.

Sexual development of the malaria parasites involves the female or "macrogametocyte" and the male parasite or "microgametocyte." These gametocytes do not undergo any further development in man. Upon ingestion of the gametocytes into the mosquito, the complicated sexual cycle begins in the midgut of the mosquito. The red blood cells disintegrate in the midgut of the mosquito after 10 to 20 minutes. The microgametocyte continues to develop through exflagellation and releases 8 highly flagellated microgametes. Fertilization occurs with the fusion of the microgamete into a macrogamete. The fertilized parasite is known as a zygote that develops into an "ookinete." The ookinete penetrates the midgut wall of the mosquito and transforms into the oocyst within which many small sporozoites form. When the oocyst ruptures the sporozoites migrate to the salivary gland of the mosquito via the hemolymph. Once in the saliva of the mosquito, the parasite can be injected into a host.

Malaria vaccines are being developed against different stages in the parasite's life-cycle including the sporozoite, asexual erythrocyte, and sexual stage. Each development increases the opportunity to control malaria in the many diverse settings within which the disease occurs. Sporozoite vaccines would prevent mosquito-induced infections. First generation vaccines of this type have been tested in humans. Asexual erythrocytic stage vaccines would be useful in reducing the severity of the disease. Multiple candidate antigens have been cloned and tested in animals and in humans.

One type of vaccine being investigated to slow or reverse the worsening epidemic of malaria is a transmission-blocking vaccine [Miller et al., *Science* 234:1349 (1988)]. Transmission of *Plasmodium falciparum* from host to mosquito vector can be blocked by monoclonal antibodies against a 25 kDa sexual stage surface protein, Pfs25, expressed on zygotes and ookinetes [Vermeulen et al., *J. Exp. Med.* 162:1460 (1985)]. The gene encoding Pfs25 has been cloned [Kaslow et al., *Nature* 333:74 (1988)], and the deduced amino acid sequence revealed a striking feature, the presence of four tandem epidermal growth factor (EGF)-like domains. EGF-like domains are cysteine rich and depend on proper disulfide bond formation for structural integrity [Savage et al., *J. Biol. Chem.* 247:7612 (1972)]. Of the monoclonal antibodies previously known to block transmission, none recognize the reduced Pfs25 antigen [Vermeulen et al., *J. Exp. Med.* 162:1460 (1985) and Carter et al., *Prog. Allergy* 41:193 (1988)), suggesting that for at least some of the blocking epitopes, disulfide bonds are involved in creating proper conformation.

Before Pfs25 can be used as an effective transmission-blocking vaccine, peptides or recombinant DNA-derived Pfs25 molecules having the appropriate conformation for immunological activity in vivo must be produced in large quantities. In addition, adjuvant formulations must be developed which are suitable for use in human transmission-blocking vaccines.

SUMMARY OF THE INVENTION

Accordingly, it is an object of the present invention to provide large quantities of Pfs25 or an analogue thereof which elicit transmission-blocking antibodies.

It is another object of the present invention to provide a transmission-blocking vaccine.

Various other objects and advantages of the present invention will become apparent from the following description of the invention together with the figures.

BRIEF DESCRIPTION OF THE DRAWINGS

FIG. 2 shows antibody titres of Aotus monkeys immunized with Pfs25-B and MTP-MF59 adjuvant. Monkeys were injected intramuscularly at four weekly intervals (↓).

DETAILED DESCRIPTION OF THE INVENTION

Figure 1A:
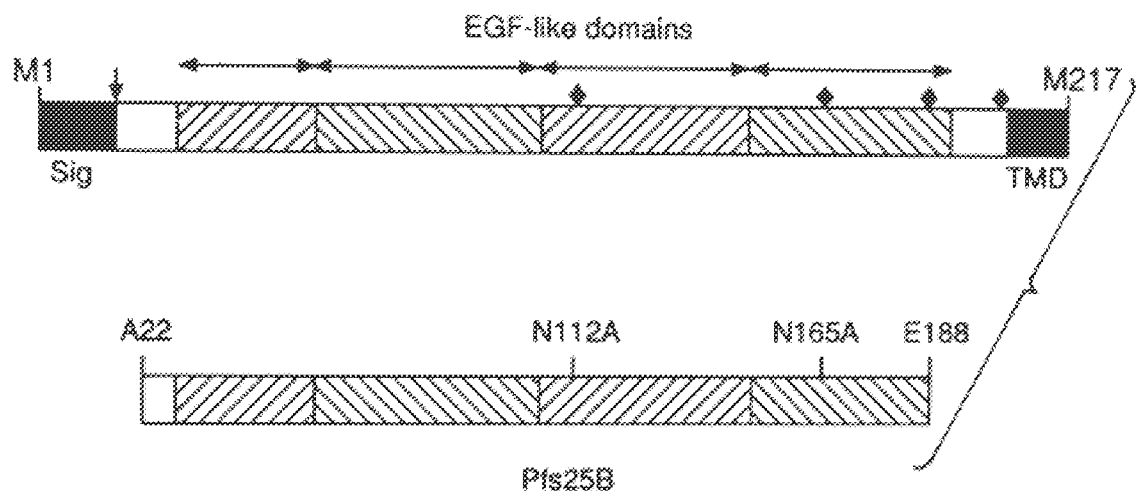
FIGS. 1A & B shows a schematic representation of the natural 217 amino acid Pfs25 protein and the yeast recombinant Pfs25-B. Shown are the four regions with sequence homology to EGF (hatched and arrowed), potential N-linked glycosylation sites (♦), a putative signal peptide sequence (Sig) and consensus signal peptidase cleavage site (↓). The hydrophobic transmembrane domain (TMD) that serves as an attachment signal for the glycosylphosphatidyl-inositol anchor is also shown.

The present invention relates to transmission-blocking vaccines against malaria. From these studies, it was determined that yeast-produced Pfs25 elicits the production of transmission-blocking antibodies. The present inventors have engineered, by chemical synthesis and mutagenesis, a gene and expressed same in yeast cells to produce an analogue of Pfs25, designated Pfs25-B. Absent from the yeast-expressed protein was the amino-terminal secretory sequence and the hydrophobic carboxyl terminal region. The N-linked glycosylation sites were also removed from Pfs25-B. Pfs25-B was shown to react with conformation dependent monoclonal antibodies despite its conformational changes. In addition, Pfs25-B elicited transmission-blocking activity in mice and monkeys.

Accordingly, the present invention relates to recombinant DNA constructs encoding a 25 kDa sexual stage surface protein, Pfs25, from *Plasmodium falciparum* which lacks the amino-terminal secretory signal and the hydrophobic carboxyl-terminal region. The encoded protein may also lack one or more N-linked glycosylation sites. The DNA segment encoding the protein is operably linked to a vector, for example, pBS24-Pfs25-B. The DNA segment encoding the Pfs25 analogue is exemplified by Pfs25-B gene, however, other genes can be synthesized using methods known in the art.

The present invention also relates to yeast cells transfected with the recombinant construct of the present invention. Suitable yeast cells for use in the present invention include, but are not limited to AB110. Yeast cells of the present invention are grown under conditions such that the Pfs25 analogue is expressed. The yeast-produced Pfs25 of the present invention is purified using methods known in the art, for example, ion-exchange and sizing column chromatography. The product can be used to induce anti-Pfs25 antibodies in mammals, such as mice, monkeys or humans.

The present invention further relates to transmission-blocking vaccines against malaria. A transmission-blocking vaccine prevents the transmission of *Plasmodium falciparum* from host to mosquito vector. The present invention provides a yeast-produced protein which elicits transmission-blocking antibodies in both mice and monkeys.

Transmission-blocking vaccines of the present invention comprise the yeast-expressed Pfs25 protein or analogue thereof present in an amount sufficient to induce immunization against malaria. The vaccine can further comprise an adjuvant, such as, for example, MTP-MF59 or alum. The vaccine can be administered via intradermal, subcutaneous, intramuscular, nasopharyngeal or respiratory routes, for example, inhalation.

The transmission-blocking vaccines of the present invention can also include other malarial antigens. For example, the transmission-blocking vaccine of the present invention include antigens generating protective malarial immunity.

The present invention also relates to methods of preventing transmission of malarial infections. Methods of the present invention comprise administering to a patient a vaccine of the present invention in an amount sufficient to induce transmission-blocking activity. The treatment consists of a single administration or a series of administrations. When given as a series administrations, inoculations subsequent to the initial administration are given to boost the immune response and may be referred to as booster inoculations.

The treatment given will vary in the number of inoculations and the vaccine used depending on several factors, such as the patient's conditions and the route of administration. These factors are easily assessed by the physician and an appropriate treatment determined therefrom.

The following examples are given to further illustrate the present invention without being deemed limitative thereof.

EXAMPLES

A Pfs25 gene encoding amino acids 22 to 190 of the natural 217 amino acid precursor protein was chemically synthesized using methods previously disclosed (e.g., Barr et al, J. Biol. Chem. (1988) 263:16471–16478]. The synthesized gene lacked the proposed amino-terminal secretory sequence of the Pfs25 protein and the hydrophobic carboxyl-terminal region that has been proposed to serve as a signal for attachment of the glycosylphosphatidyl-inositol membrane anchor.

Expression and secretion from yeast (AB110, see Barr et al, J. Biol. Chem. (1988) 263:16471–16478) of the synthesized Pfs25 extracellular domain was achieved by fusion of the synthetic gene to DNA sequences encoding the yeast α-factor pheromone secretory signal/leader sequence [Brake et al, Proc. Natl. Acad. Sci. U.S.A. 81:4642 (1984)]. Transcription of the Pfs25 gene was driven by the glucose-regulated ADH2/GAPHDH hybrid promoter previously described [Shuster et al., *In Yeast Genetic Engineerinq*].

A second gene was also constructed, in which the three remaining N-linked glycosylation sites at amino acid positions 112, 165 and 187 of the encoded protein (see FIG. 1A) were removed by Asn-Ala mutation and introduction of a termination codon after Glu188. The mutation was carried out using: i) standard M13 mutagenesis procedure (Maniatis et al (1982) Molecular Cloning, A Laboratory Manual, Cold Spring Harbor Laboratory Manual, Cold Spring Harbor, N.Y.), or ii) the polymerase chain reaction. This gene was introduced into a pBS24 plasmid [Barr et al Molecular and Biochemical Parasitology (1991) 47:159–170] using standard methods. The protein produced by the construct was designated Pfs25-B. The removal of the glycosylation sites allowed the secretion from yeast of a homogeneous product that also contained all four epidermal growth factor (EGF)-like repeats described previously for Pfs25 (see FIG. 1A) [Kaslow, D.C., Nature 333:74 (1988)].

Figure 1B:
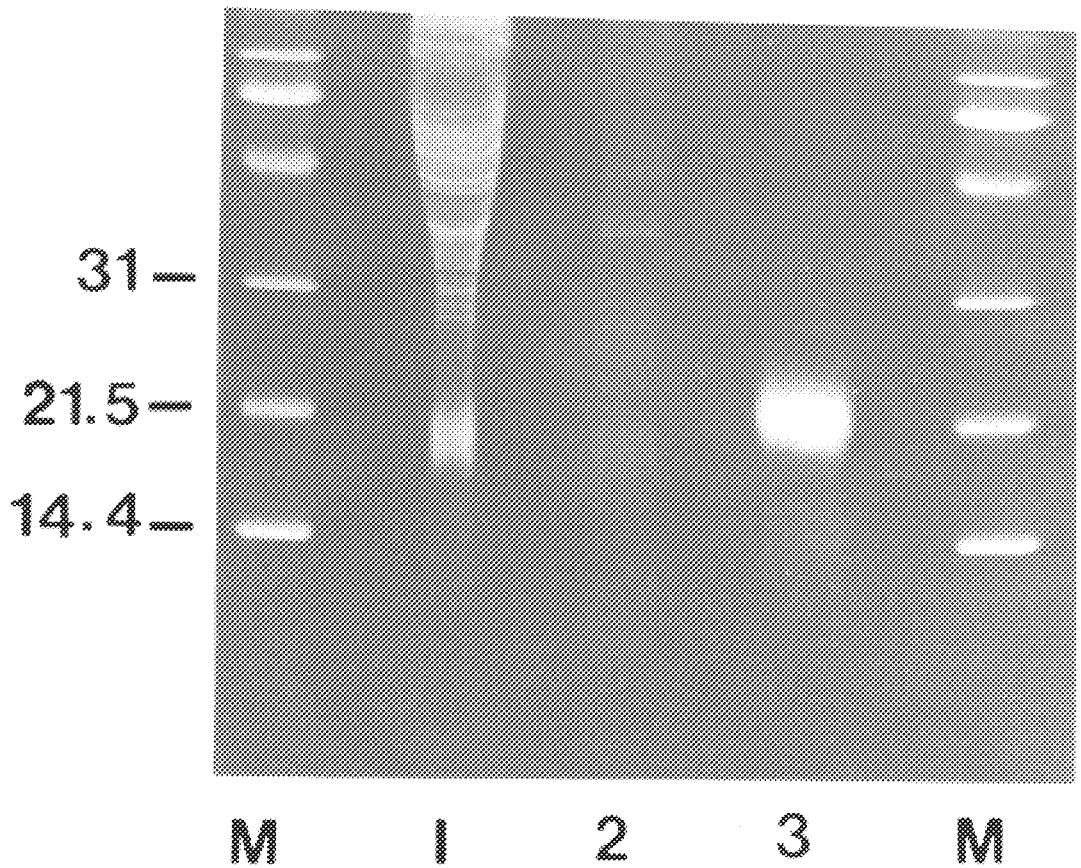

Yeast cells (AB110) were transformed with the plasmid pBS24-Pfs25-B by the spherophast method [Hinnen et al (1978) Proc. Natl. Acad. Sci. USA 75:1919–1933]. The cells were then cultured/grown as described by Barr et al [J. Biol. Chem. (1988) 263:16741–16478]. The yeast secreted Pfs25-B protein (See FIG. 1B) was purified by gel filtration on S-100 HR (Pharmacia) and analyzed by immunoblotting using rabbit polyclonal antisera to Pfs25 or with the monoclonal antibody (MAb) 1C7 [Kaslow, D. C., Nature 333:74 (1988)], a transmission-blocking MAb that had been shown previously to recognize natural Pfs25 only under non-denaturing conditions.

The purified protein was used to immunize mice (Swiss-Webster) and *Aotus trivirgatus* monkeys together with the muramyl tripeptide (MTP) adjuvant MF59. The MF59 adjuvant has been used previously to elicit high antibody titres in rodents and goats with other recombinant malaria proteins. MF59 has also been demonstrated to be safe and efficacious in humans when used in conjunction with a yeast-derived human immunodeficiency virus-1 (HIV-1) envelope protein [Abrignani et al., Proc. Natl. Acad. Sci. U.S.A. 87:6136 (1990)].

Mice were immunized with Freunds adjuvant plus Pfs25-B or MF59 plus Pfs25-B. In the Freunds adjuvant group, mice were immunized three times at three weekly intervals with 50 ug of Pfs25-B in a final volume of 100 $\mu$l as described previously. In the MF59 adjuvant groups, mice were immunized, using the same protocol with Pfs25-B, falc 2.3, hEGF or hSOD (50 ug per injection). Animals were bled one week after the final immunization and antibody titres were measured in the ELISA format as described previously [see Table 7 below].

Monkeys were injected intramuscularly with three 100 $\mu$g doses of Pfs25-B in MF59 at four weekly intervals (see FIG.

2). Titres were measured by ELISA every two weeks and sera taken at weeks 0, 12 and 22 were used for mosquito feeding experiments described below.

Humoral immune responses elicited in mice with both Freunds adjuvant and MF59 (see Table 1 below) were measured by ELISA. Also shown in Table 1 are the reactivities of antisera raised with recombinant Pfs25 against various control recombinant proteins from yeast. These include, human superoxide dismutase (hSOD) [Hallewell et al., Biotechnology 5:363 (1987)], a circumsporozoite (CS) protein from P. falciparum (falc 2.3), and human EGF [Brake et al., Proc. Natl. Acad. Sci. U.S.A. 81:4642 (1984) and George-Nascimento et al., Biochemistry 27:797 (1988)].

TABLE 1

Antibody titres developed in mice by immunization with recombinant Pfs25-B and either Freunds (FCA\FIA) or MF59 adjuvants.

| | | Assay Protein | | | |
|---|---|---|---|---|---|
| Antigen | Adjuvant | Pfs 25B | Falc 2.3 | hEGF | hSOD |
| Pfs25-B | FCA/FIA | 42,000 | <100 | <100 | <100 |
| Pfs25-B | MF59 | 31,625 | <100 | <100 | <100 |
| Falc 2.3 | MF59 | <100 | 20,200 | <100 | ND |
| hEGF | MF59 | <100 | <100 | 9,100 | ND |
| hOSD | MF59 | <100 | ND | <100 | 18,750 |

ND = Not determined

The ability of sera to block the formation of oocysts in P. falciparum gametocyte-fed mosquitoes was determined as described previously [Quakyi et al., J. Immunol. 139:4213 (1987)]. The results are shown below in Table 2A.

Briefly, sera from mice immunized with Pfs25-B or falc 2.3 (as described above) were assayed for transmission-blocking activity and compared with the Mab 1D3. Mosquitoes were fed on either the mouse sera or Mab ascites fluid at a 1:2 dilution of the feed [Quakyi et al., J. Immunol. 139:4213–4217 (1987)]. Mosquitoes were dissected after 7–8 days, and the numbers of infected mosquitoes and oocysts determined. Infectivity was scored as the number of oocysts found in the sample divided by the number found in the pooled prebleed control X100%.

Murine antisera against Pfs25-B from either Freunds or MF569-adjuvanted mice were able to dramatically reduce or even abolish the sexual development of the parasite within the mosquito mid gut. Only one oocyst was detected in 37 mosquitoes dissected from the immune sera groups, whereas all 16 control, preimmune sera-fed mosquitoes developed oocysts, with an average number of 8 per mosquito. This is comparable with results obtained using the transmission-blocking MAb 1D3. This MAb, at a dilution of 1:2 of ascites fluid, fully blocked oocyst development in all 16 mosquitoes tested (see Table 2A).

Similarly, sera from two A. trivirgatus monkeys were capable of blocking completely the development of oocysts in mosquitoes after immunization with Pfs25-B. The ability of the sera to block oocyst development was measured as above. Prebleed sera from each monkey (numbers A108 and A142) were used as controls. Transmission-blocking activities were measured at 12 and 22 weeks. Mabs 1D2 and 4B7 were also shown to block oocyst appearance at a 1:2 dilution, whereas sera from the two monkeys that were injected with MF59 alone failed to inhibit oocyst development at any of the bleeds assayed. This transmission-blocking activity persisted for nearly 4 months in one monkey and more than 6 months in the other (see Table 2B below).

TABLE 2

Inhibition of oocyst development by sera from immunized animals.

| Sample | Mean Oocyst Numbers (Range) | Infectivity % of Control | Mosq. Infected Mosq. Dissected |
|---|---|---|---|
| A | | | |
| Pooled Preimmune | 8 (1–22) | 100% | 16/16 |
| Pfs25-B (CFA/IFA) | 0 (0–1) | <1% | 1/19 |
| Pfs25-B (MF59) | 0 (0) | 0% | 0/18 |
| Falc 2.3 (MF59) | 4 (0–13) | 50% | 17/18 |
| Mab 103 | 0 (0) | 0% | 0/16 |
| B | | | |
| A108 Preimmune | 39 (0–89) | 100% | 20/21 |
| A142 Preimmune | 25 (5–75) | 100% | 21/21 |
| A108 Week 12 | 0 (0–1) | <1% | 1/24 |
| A142 Week 12 | 0 (0) | 0% | 0/20 |
| A108 Week 22 | 0 (0) | 0% | 0/28 |
| A142 Week 22 | 2.6 (0–35) | 10% | 15/26 |
| Mab 102 | 0 (0–1) | <1% | 1/20 |
| Mab 487 | 0 (0) | 0% | 0/24 |

Figure 3A:
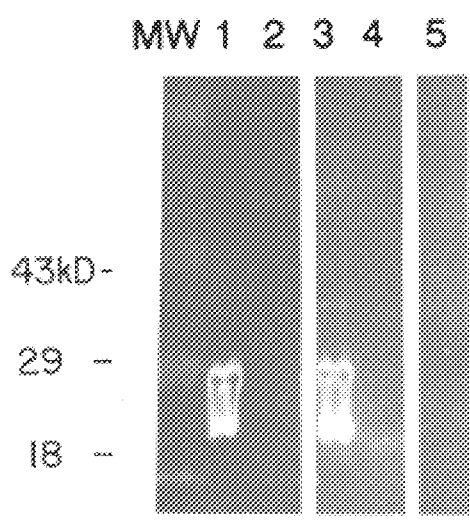
FIGS. 3A & B shows an immunoblot analysis of Pfs25-B conformation. Lanes 2,4 and 5: Pfs25-B, Lanes 1 and 3: native Pfs25, Lanes 1 and 2: MAb 1D2, Lanes 3 and 4: MAb 4B7, Lane 5: antisera P7 MW, prestained protein markers in kDa (BRL).
Figure 3B:
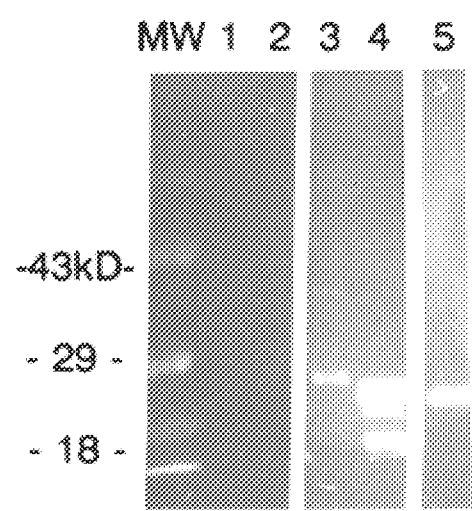

Conformation-dependent antibodies did not react as strongly with Pfs25-B as with native Pfs25 (See FIG. 3). Pfs25-B (10 µg per lane) and native Pfs25 (Titron X-100 extract from $5 \times 10^6$ 5 hr zygotes per lane), were fractionated by 4–20% SDS-PAGE in the presence (reduced) or absence (nonreduced) of 5% 2-mercaptoethanol and electroblotted to nitrocellulose as previously described [Quakyi et al., J. Immunol. 139:4213–4217 (1987)]. Binding of a 1:200 dilution of MAb 1D2 (lanes 1 and 2), Mab 4B7 (lanes 3 and 4), or antisera P7 (lane 5) was detected by alkaline phosphatase-labeled goat anti-mouse sera (PlcoBlue, Stratagene).

MAB 4B7 was a product of a fusion of spleen cells from a BALB/c mouse immunized twice with recombinant vaccinia virus that were expressing Pfs25 and boosted with whole P. falciparum gametes. Supernatants from the fusion were screened for specificity to Pfs25 by immunoblot of reduced Pfs25-B. Antisera P7 was produced from mice immunized with synthetic peptides derived from the deduced amino acid sequences of Pfs25 [Kaslow et al., Nature 333:74–76 (1988)].

Conformational integrity has been shown to be extremely important for the recognition, by antibodies, of epitopes of Pfs25 that block transmission. Surprisingly, the conformation-dependent neutralizing MAbs 1C7, 1D2 and 1D3 [Kaslow et al., Nature 333:74–76 (1988)] that are known to react with the same epitope of Pfs25 [Quakyi et al., J. Immunol. 139:4213–4217 (1987)] did not react as strongly with the secreted recombinant Pfs25-B as they did with native Pfs25 on non-reducing SDS-PAGE immunoblots (see FIG. 3). Although the related six cysteine residue-containing hEGF has been shown to be correctly folded and disulfide-linked when using this expression system [Brake et al., Proc. Natl. Acad. Sci. U.S.A. 81:4642–4646 (1984) and George-Nascimento et al., Biochemistry 27:797–802 (1988)], recombinant Pfs25-B with four EGF-like repeats and twenty-two cysteine residues may possess only partial structural integrity. Pfs25-B also lacked the glycosylphosphatidyl-inositol anchor that is characteristic of the native Pfs25 molecule [Fries et al., *Parasite Immunol.* 11:31–45 (1989)].

As the epitope recognized by the conformation-dependent neutralizing MAb 1D2 is destroyed by reduction (see FIG. 3), but not by SDS, varying salt concentrations, or extremes of pH, the reactivity of Mab 1D2 against recombinant Pfs25-B is a sensitive assay for proper disulfide bond formation at or about the Mab 1D2 epitope. The very weak reactivity of Mab 1D2 with secreted Pfs25-B suggests that the 1D2 epitope is not completely recreated in this recombinant protein. Post-translational modification differences could explain these findings. In addition, these findings can be explained by improper disulfide bond formation.

Antisera P7, generated against a group of synthetic peptides of Pfs25 recognizes only fully reduced native protein and, therefore, serves to assay for the complete absence of disulfide bonds. P7 reacts with Pfs25-B on reducing but not on nonreducing SDS-PAGE immunoblots, demonstrating that Pfs25-B contains disulfide bonds. Also, 4B7, a previously undescribed Mab to Pfs25, that reacts quite strongly with nonreduced Pfs25 and weakly with reduced Pfs25, clearly reacted with nonreduced Pfs25-B with the reactivity increasing markedly upon reduction of Pfs25-B (see FIG. 3). These data suggest that the Mab 4B7 epitope is also improperly formed in Pfs25-B and that the reduced reactivity with Pfs25-B as compared to parasite-produced Pfs25 is not a result of post-translational modification.

Antibodies that recognize reduced Pfs25, such as Mab 4B7, were shown to block transmission (see Table 2), suggesting that epitopes that are not dependent on disulfide bonds for conformation may elicit transmission-blocking antibodies. Despite this, however, the yeast-derived Pfs25-B of the present invention was fully capable of inducing transmission-blocking immunity in both mice and monkeys. In addition, transmission-blocking antisera did not recognize recombinant hEGF in an ELISA assay (see Table 1), nor did antisera to hEGF recognize Pfs25-B in such an assay (see Table 1). The cross-reactivity of antisera to hEGF with Pfs25-B was also below the limit of detection. The homology of Pfs25 to EGF might give rise to an auto-immune response in individuals immunized with Pfs25. Data, however, indicates that this is not likely to be the case. It is anticipated that this lack of cross-reactivity will be similar for other members of the polypeptide family that contain EGF-like motifs and are, therefore, not likely to be a concern in transmission-blocking vaccination studies with Pfs25.

Several recombinant DNA-derived antigens or synthetic peptides of malaria parasites have been shown to be only weakly immunogenic in humans [Herrington et al., *Nature* 328:257–259 (1987) and Gordon et al., *Am. J. Trop. Med. and Hyg.* 42:527–531 (1990)]. Since Pfs25 is not expressed at the gametocyte stage, but appears only during sexual development in the mosquito, and has, therefore, not been subjected to immune pressure in the human host, it is anticipated that the immunogenicity of Pfs25-B in humans will closely parallel that observed in experimental animals. Furthermore, transmission-blocking immunity elicited in both mice and monkeys was observed with MTP-MF59, an adjuvant that has been shown previously to be safe and efficacious in humans [Abrignani et al., *Proc. Natl. Acad. Sci. U.S.A.* 87:6136–6140 (1990)]. Based on the extremely high yields of the Pfs25 protein that can be obtained from yeast, together with the immunogenicity data, the combination of Pfs25 from yeast and MTP-MF59 represents an excellent initial formulation for the study of transmission-blocking immunity in humans.

All references cited hereinabove are hereby incorporated by reference.

While the foregoing invention has been described in some detail for purposes of clarity and understanding, it will be appreciated by one skilled in the art from a reading of this disclosure that various changes in form and detail can be made without departing from the scope of the invention.

What is claimed is:

1. A vaccine for reducing the sexual development of *Plasmodium falciparum* within a mosquito comprising a Pfs25 *Plasmodium falciparum* protein, wherein the Pfs25 protein lacks a native N-terminal secretory sequence and a native hydrophobic carboxy-terminal region, wherein vaccine elicits antibodies that recognize the Pfs25 *Plasmodium falciparum* protein and the antibodies are capable of reducing the sexual development of *Plasmodium falciparum* within a mosquito.

2. The vaccine according to claim 1 which further comprises an adjuvant.

3. The vaccine according to claim 2 wherein said adjuvant is selected from the group consisting of alum and MTP-MF59.

4. The vaccine according to claim 1 wherein said Pfs25 *Plasmodium falciparum* protein comprises residues 22 to 190.

5. The vaccine according to claim 1, wherein said Pfs25 *Plasmodium falciparum* protein further comprises a yeast alpha-factor pheromone signal/leader sequence.

6. The vaccine according to claim 1, wherein transcription of a gene encoding said Pfs25 *Plasmodium falciparum* protein is controlled by a glucose-regulated ADH2/GAPHDH (alcohol dehydrogenase-2/Glyceraldehyde-3-phoshate dehydrogenase) hybrid promoter.

7. The vaccine according to claim 1, wherein said Pfs25 *Plasmodium falciparum* protein wherein at least one N-linked glycosylation site amino acid residue has been mutated to encode for another amino acid residue, thereby removing the glycosylation site.

8. The vaccine according to claim 7, wherein said missing N-linked glycosylation site is selected from the group consisting of an amino acid site at position 112, an amino acid site at position 165 and an amino acid site at position 187.

9. The vaccine according to claim 7, wherein said mutated amino acid residue is an alanine or glutamine.

10. The vaccine according to claim 1, wherein said Pfs25 *Plasmodium falciparum* protein has a termination codon inserted after a glutamine at position 188.

11. The method of claim 10, wherein the administration of the vaccine comprises inoculations subsequent to an initial administration of the vaccine.

12. The vaccine according to claim 1, wherein the vaccine further comprises other protective malarial antigens.

13. A method of reducing the sexual development of *Plasmodium falciparum* within a mosquito, comprising administering to an individual the vaccine of claim 1, in an amount sufficient to elicit antibodies in the individual that recognize the Pfs25 *Plasmodium falciparum* protein.

* * * * *